United States Patent [19]

Glazar

[11] 4,113,211
[45] Sep. 12, 1978

[54] HOT BOX DETECTOR BEARING DISCRIMINATOR CIRCUIT

[75] Inventor: Arthur J. Glazar, Kings Park, N.Y.

[73] Assignee: Servo Corporation of America, Hicksville, N.Y.

[21] Appl. No.: 841,700

[22] Filed: Oct. 13, 1977

[51] Int. Cl.² .............................................. B61K 9/04
[52] U.S. Cl. ....................... 246/169 A; 116/DIG. 38; 308/1 A; 340/47
[58] Field of Search ........ 246/169 A, 169 D, DIG. 1, 246/DIG. 2; 116/DIG. 38, 101, 114.5; 308/1 A; 340/231, 269

[56] References Cited

U.S. PATENT DOCUMENTS 3,812,343  5/1974  Gallagher ........................ 246/169 D Primary Examiner—Trygve M. Blix
Assistant Examiner—Reinhard J. Eisenzopf
Attorney, Agent, or Firm—Kane, Dalsimer, Kane, Sullivan and Kurucz

[57] ABSTRACT

An improved circuit is provided for differentiating between roller bearings and friction bearings in a railroad hot box detector system. The improved circuit integrates the waveform generated by a bearing scanner and compares that to the integral of a pre-selected portion of the waveform. By this method of comparison, irregularities in the system due to noise are obviated.

5 Claims, 4 Drawing Figures

HOT BOX DETECTOR BEARING DISCRIMINATOR CIRCUIT

BACKGROUND OF THE INVENTION

The present invention relates to railroad car hot box detectors and more particularly to an improved bearing discriminator circuit for discriminating between readings from roller bearings and friction bearings.

In order to protect against railroad car wheel bearing failure, railroads utilize hot box scanners along their rights of way to scan, through infrared sensitive viewers, the bearings of passing railroad cars. In the event an overheated bearing is detected, the train engineer receives a signal to stop the train and correct the condition before a bearing faiure and possible derailment can occur. Since the unscheduled stopping of a railroad train is a costly and time consuming operation and can totally disrupt schedules it is obviously desirable to enhance as much as possible the accuracy of such hot box detectors.

One problem faced by the designers of hot box detectors is that railroad car wheel bearings are either of the roller bearing or friction bearing (known also as solid and sleeve bearings) variety. While all the bearings on any particular car usually are of the same type, the bearings typically differ from car to car and train to train. Due to physical differences between roller and friction bearings, the output signals from roller bearings are significantly higher (all other factors being equal) than signals from friction bearings. Thus, automatic alarm systems that are based upon amplitude detection must contend with a range of amplitudes that is common to both normal roller bearings and to overheated plain bearings. A discussion of the problems associated with roller-friction bearing discrimination is contained in U.S. Pat. No. 3,812,343 of which I am co-inventor and which is commonly assigned with the present application.

As discussed in the above mentioned patent, it has been observed that there are characteristic differences between the wave shapes and signals generated by passing roller bearings and friction bearings when scanned by a hot box detector such as the SERVOSAFE hot box detective system marketed by the Servo Corporation of America, Hicksville, New York. As shown from FIG. 1, the ideal waveforms of roller and friction bearings may readily be distinguished from one another. Primarily, roller bearing waveforms ideally are generally trapezoidal whereas the friction bearing waveform is sawtooth in shape. Heretofore, discrimination between roller and friction bearings was attained by picking a point in space on every waveform (such as a ½ width point) and comparing the amplitude of the waveform at that point with the maximum amplitude. Ideally, for roller bearings the ratio of the maximum value to sample point should be 1:1, while for friction bearings, the ratio should be greater than 1:1. In practice, a ratio of 1.4:1 has been used. While this arrangement has been successfully employed, it can have serious problems when noisy signals are generated. In practice, the roller bearing waveform may often take one of the shapes shown in FIG. 2 with one or more noise generated spikes or notches. The hot box detector system must be able to distinguish between a noisy signal generated from a properly operated roller bearing or an overheat signal generated from a hot friction bearing. That is, if the notch in the roller bearing waveform extends to the sample point the detector could interpret the roller bearing waveform as coming from a friction bearing and since the amplitudes are such to indicate that the friction bearing is overheated, an improper signal to stop the train could be transmitted.

In view of the above, it is the principal object of the present invention to provide an improved discriminator circuit for a hot box detector system.

A further object is to provide such a circuit which can distinguish between signals generated by roller bearings and friction bearings with high probability of success.

A still further object is to provide such a circuit which is relatively simple to produce and may readily be retrofitted into existing equipment.

SUMMARY OF THE INVENTION

The above and other beneficial objects and advantages are attained in accordance with the present invention by providing a railroad hot box detector system of the type including a heat responsive scanner associated with a section of track adapted to scan bearings of a railroad car on the section of track and to generate an output signal in response thereto having an amplitude and waveform indicative of the temperature of and type of bearing being scanned.

The system further includes sensor means adapted to generate a first signal when a bearing enters the field of view of the scanner, a second signal when the bearing leaves the field of view of the scanner and a third signal representing a preselected portion of the overall waveform. The signal from the scanner is fed to a voltage controlled current source whose output current charges a pair of capacitors through steering gates. The voltage on each capacitor thus is the time integral of the scanner signal evaluated during the time period that the gate is activated. The first capacitor integrates over the period of the entire waveform as determined by the first and second signals. The second capacitor integrates the waveform over a preselected timewise portion of the waveform period as determined by the third signal. The integrated waveform signals are then fed to a comparator wherein the ratio is used to determine whether the scanner is viewing a roller bearing or friction bearing.

BRIEF DESCRIPTION OF THE DRAWINGS

In the accompanying drawings:

FIG. 2 is a diagram similar to FIG. 1 depicting such waveforms as they are modified by noise and the like;

DETAILED DESCRIPTION OF THE PREFERRED EMBODIMENT

Figure 1:
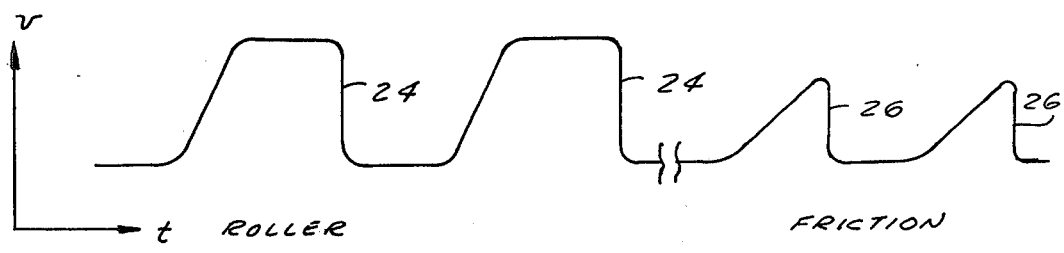
FIG. 1 is an idealized diagram of the output waveforms of a hot box detector scanner.
Figure 3:
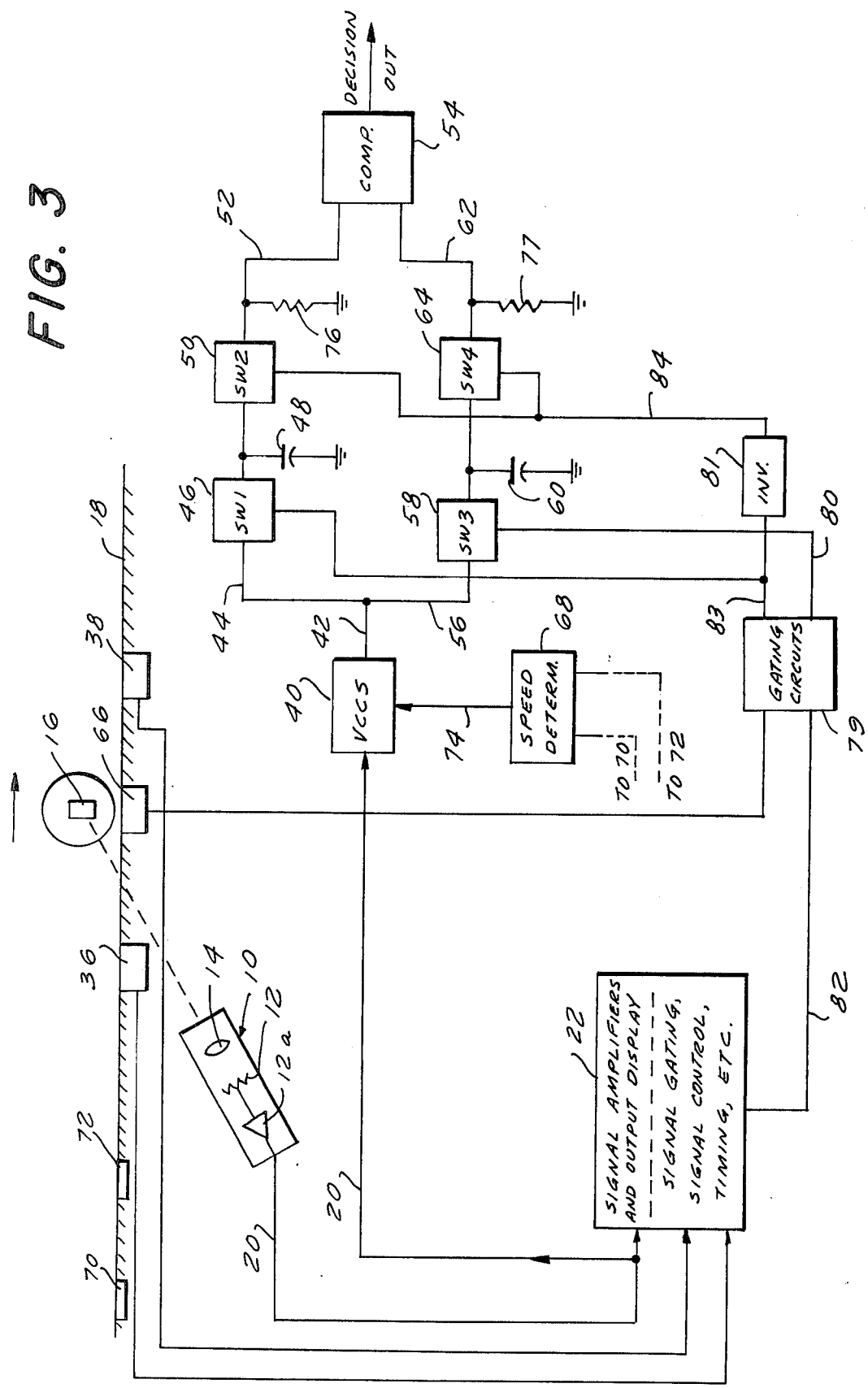
FIG. 3 is a schematic representation of the improved discriminating circuit of the present invention; and, FIG. 4 depicts the nature of the control signals at various points in the circuit.

Reference is now made to the drawings and to FIG. 3 in particular wherein a discriminating circuit in accordance with the present invention is shown connected (as much as is necessary for purposes of the present description) with a conventional hot box detector system such as the previously mentioned SERVOSAFE HOT BOX DETECTIVE system of the Servo Corporation of America of Hicksville, New York. The detector system includes a scanner 10 having an infrared sensor 12 and preamplifier 12a. Radiation from a passing wheel is imaged through suitable optics 14 permitting the scanner to "view" the bearings 16 of trains passing along a section of track 18. The output of scanner 10 is fed along line 20 to the electronics of a standard hot box detector system 22 such as that marketed by the previously mentioned Servo Corporation of America. Ideally, for a passing roller bearing, the signal along line 20 would be generally of the shape depicted by waveforms 24 of FIG. 1. Similarly, for a passing friction bearing, the waveforms would be of the shape depicted by waveforms 26 of FIG. 1.

Figure 2:
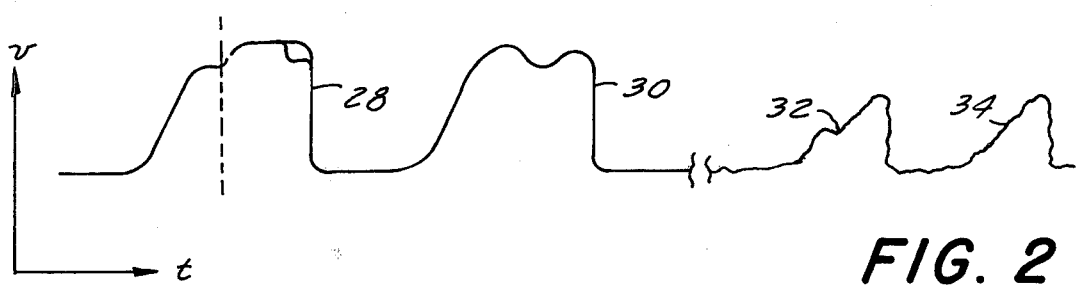

Due to noise factors, the signal from a passing roller bearing may be of the shape of waveforms 28 or 30 of FIG. 2. That is, a notched section of the ideal waveform 25 might be lost during transmission. Similarly, the actual waveform for a friction bearing is shown by the sawtooth waves 32 and 34 of FIG. 2. As previously explained, while the waveforms of roller and friction bearing scans may readily be differentiated under normal circumstances in an extreme case, a normally operating roller bearing may generate a distorted waveform which could be interpreted by a waveform analyzing circuit of the type discussed above as if an overheated friction bearing had generated the waveform.

In accordance with the present invention, the output of scanner 10 is fed to a voltage controlled current source 40, which in turn produces an output current proportional to the input voltage. The output of current source 40 is fed through lines 42 and 44 through switch 46 to charge a capacitor 48. Switch 46 closes when wheel sensor 36 indicates that a wheel has passed it. When the wheel passes the second sensor 38, switch 46 opens and a second switch 50 closes connecting charged capacitor 48 with one input 52 of a comparator 54. Thus, capacitor 48 charges while the wheel is between sensors 36 and 38 and discharges through comparator 54 immediately after the wheel passes sensor 38. The capacitor 48 thus acts to integrate the waveform of the scanner output for the period that a wheel bearing is within the field of view of the scanner.

The output of current source 40 is also fed through lines 42 and 56 and switch 58 to charge a second capacitor 60 during the period the wheel is between wheel sensors 36 and 66. That is, wheel sensor 36 serves to close switch 58 when the wheel passes. Capacitor 60 is connected to a second input 62 of comparator 54 through switch 64. Switch 64 operates in unison with switch 50. The interval during which capacitor 60 charges may be selected mechanically as for example by placing a third wheel sensor 66 between wheel sensors 36 and 38. Alternately, the portion may be determined timewise. The capacitor 60 thus serves to integrate the portion of the waveform of the output of the scanner for the preselected portion of the waveform period. When switch 50 closes, capacitor 48 discharges through resistor 76 via switch 50. The resulting voltage developed across resistor 76 is applied to comparator input 52.

Figure 4:
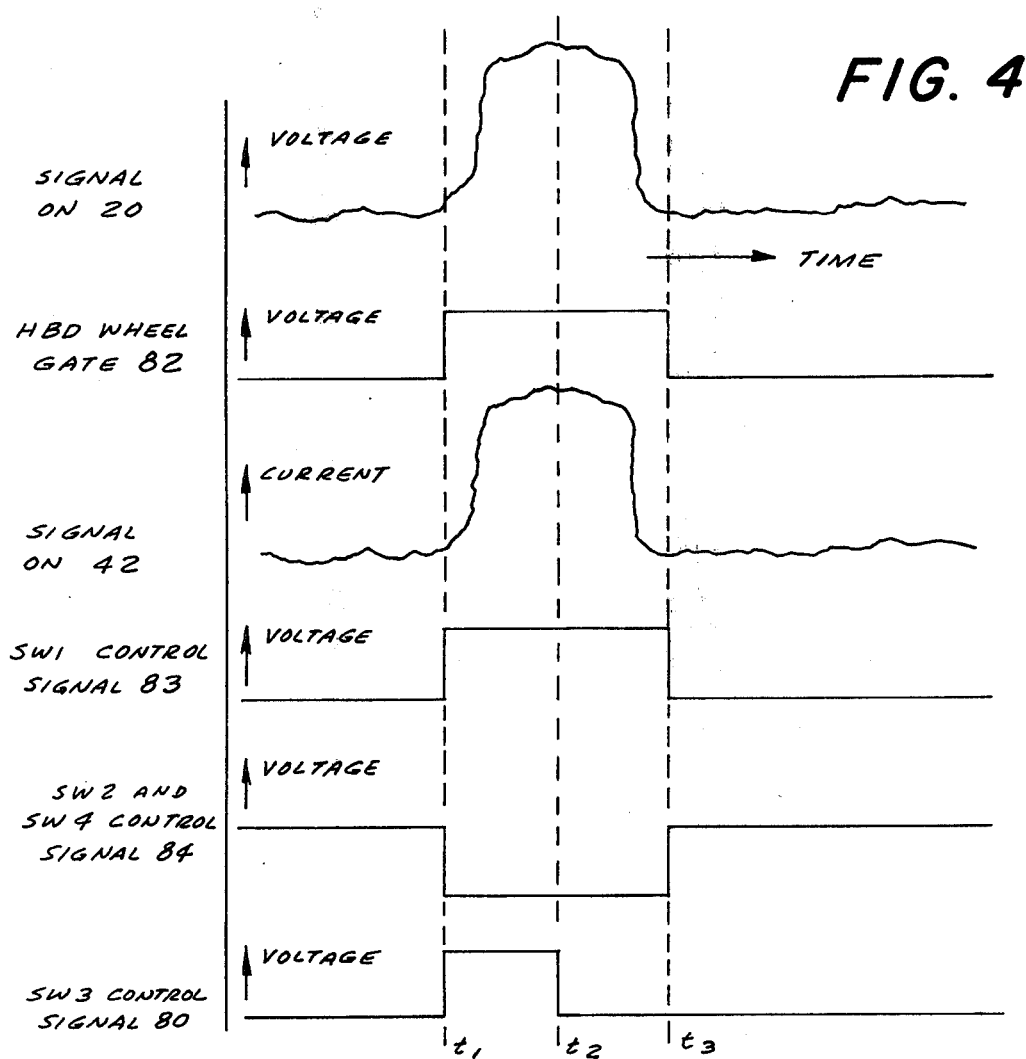

The control signals for switches 46, 50, 58 and 64 are obtained from wheel sensors 36 and 38 through the detector system 22 and line 82 to gating circuit 79. A signal from sensor 66 is fed directly to gating circuits 79. Thus, at time $t$, when a wheel passes sensor 36 switches 46 and 58 (SW and $SW_3$) turn on. At time $t_2$ when the wheel passes sensor 66, switch 58 ($SW_3$) is turned off (SW remains on). The control signals for switches 50 and 64 ($SW_2$ and $SW_4$) are the inverse of the control for $SW_1$ and thus these switches are fed through line 84 from inverter 81 which, in turn, is fed from the output 83 of the gating circuit 79. At $t_3$ when the wheel passes sensor 38 $SW_1$ opens and simultaneously $SW_2$ and $SW_4$ close. The timing sequence is shown in FIG. 4.

When switch 64 closes (in unison with switch 50) capacitor 60 discharges through resistor 77 via switch 64. The resulting voltage developed across resistor 77 is applied to comparator input 62. The resistor-capacitor time constant is chosen so that the capacitors 48 and 60 completely discharge during the time available between wheels. (This obviates necessity for a special discharge circuit to prepare capacitors for the next wheels). Thus, the comparator 54 compares a portion of the area under a waveform of FIG. 2 with the entire area under the waveform. Since the comparison is made between areas under the waveforms rather than amplitudes, any portions of the waveform lost to noise become insignificant. Since the rise time for the waveform of a roller bearing is far sharper than the comparable rise time for a friction bearing, the first area generated by a roller bearing will be much greater than the first area generated by a friction bearing, and the output of the comparator may readily be used to generate a signal indicative of whether a passing bearing is of the roller bearing or friction bearing type. This signal can then be used to set alarm levels.

Since it is impossible to determine in advance at what speed a train will pass scanner 10, it is desirable to render the discriminator circuit of the present invention independent of train speed. This, however, is of secondary importance since the dynamic range of the components may be chosen to encompass all practical train speeds (i.e., between 5 mph to 100 mph). Nonetheless, the system operation can be rendered essentially independent of train speed by varying the gain of VCCS 40 in accordance with the speed of the train. The speed of the train, in turn, is determined in a conventional manner utilizing a speed determinator 68 which obtains signals from a pair of wheel sensors 70 and 72 placed upstream of the first wheel sensor 36. That is, the time required for a train wheel to pass from wheel sensor 70 to 72 is used by the speed determinator 68 to generate an output signal along line 74 to vary the gain of the voltage controlled current source 40. In this manner, the output of the voltage controlled current source 40 becomes independent of the speed of a passing train. A second pair of wheel sensors similar to 70 and 72 may be provided downstream of sensor 38 to accommodate trains operating in the direction opposite to that shown in FIG. 3.

Thus, in accordance with the above, the aforementioned objects are effectively attained.

Having thus described the invention, what is claimed is:

1. A method of discriminating between roller bearings and friction bearings in a railroad hot box detector system comprising the steps of:
   a. scanning the bearings of a railroad car on a section of track with an infrared scanner to generate an output signal in response to and having a waveform indicative of the infrared radiation of and type of bearing scanned;
   b. feeding said waveform into a first integrating circuit to obtain a value indicative of the overall area under said waveform;
   c. feeding a preselected portion of said waveform into a second integrating circuit to obtain a value indicative of the area of the preselected portion of said waveform; and, d. comparing the outputs of the first and second integrating circuits whereby to obtain a ratio indicative of the nature of the bearing being scanned.

2. In a railroad hot box detector system of the type including: infrared responsive scanner means associated with a section of track adapted to scan bearings of a railroad car on said section of track and to generate an output signal in response thereto having an amplitude and waveform indicative of the amount of infrared radiation of and type of bearing scanned and sensor means adapted to generate a first signal when a bearing enters the field of view of said scanner and a second signal when said bearing leaves the field of view of said scanner, the improvement comprising:
   a. comparator having first and second inputs;
   b. first circuit interconnecting the output of said scanner with said comparator first input comprising:
      a first integrator;
      a first switch controlled by said sensor to connect said scanner output with said integrator when said first signal is generated; and,
      a second switch controlled by said sensor to connect said first integrator with said comparator first input when said second signal is generated;
   c. means for selecting a predetermined point in time on the waveform output signal of said scanner; and,
   d. a second circuit interconnecting the output of said scanner with said comparator second input comprising:
      a second integrator;
      a third switch controlled by said sensor to connect said scanner output with said integrator when said first signal is generated; and
      disconnecting said scanner output from said integrator when said predetermined point in time occurs; and,
      a fourth switch controlled by said selecting means for connecting said second integrator with said comparator second input when said second signal is generated.

3. The invention in accordance with claim 2 further comprising a voltage controlled current source driven by said scanner output signal and feeding said first and second circuits.

4. The invention in accordance with claim 3 further comprising means for determining the speed of a train passing the field of view of said scanner and gain control means controlling said voltage controlled current source, said last mentioned means in turn being controlled by said speed determining means.

5. The invention in accordance with claim 2 wherein said sensor means comprise first and second wheel sensors positioned on said section of track and said means for selecting a predetermined point comprises a third wheel sensor interposed between said first and second wheel sensors.

* * * * *